US006156879A

United States Patent [19]
Rome et al.

[11] Patent Number: 6,156,879
[45] Date of Patent: Dec. 5, 2000

[54] HUMAN MINOR VAULT PROTEIN P193

[75] Inventors: Leonard H. Rome, Tarzana; Valerie A. Kickhoefer, Sherman Oaks, both of Calif.

[73] Assignee: The Regents of the University of California, Oakland, Calif.

[21] Appl. No.: 09/089,621

[22] Filed: Jun. 3, 1998

[51] Int. Cl.$^7$ .............................. C07K 14/47; C12Q 1/68; G01N 3/53; A61K 38/17
[52] U.S. Cl. .............................. 530/350; 530/358; 435/6; 435/7.1; 514/2
[58] Field of Search .................................... 530/350, 358; 435/6, 7.1; 514/2

[56] References Cited

FOREIGN PATENT DOCUMENTS

WO9627611   9/1996   WIPO.

OTHER PUBLICATIONS

Kedersha, Nancy L. et al., "Vaults.III. Vault Ribonucleoprotein Particles Open into Flower–like Structures with Octagonal Symmetry," *The Journal of Cell Biology* 112(2):225–235 (1991).

Kickhoefer, Valerie A. et al., "Vaults are the answer, what is the question?" *trends in* Cell Biology 6:174–178(1996).

Ruf, Armin et al., "Structure of the catalytic fragment of poly(ADP–ribose) polymerase from chicken," *Proc. Natl. Acad. Sci. USA* 93:7481–7485 (1996).

Scheffer, George L. et al., "The drug resistance–related protein LRP is the human major vault protein," *Nature Medicine* 1(6):578–582 (1995).

Simonin Frederic et al., "The Carboxyl–terminal Domain of Human Poly(ADP–ribose) Polymerase," *The Journal of Biological Chemistry* 268:(18):13454–13461 (1993).

Sebolt–Leopold, Jr. et al. Enhancement of Alkylating Agent Activity in vitro by PD 128763, a Potent Poly(ADP–ribose) Synthetase Inhibitor. Int. J. Radiation Oncology Biol. Phys., 1992, vol. 222, pp. 619–621.

Kim, K. et al. Tumor Suppressor Gene Expression during Normal and Pathologic Myocardial Growth. J. Biol. Chem., Sep. 09, 1994, vol. 269, No. 36, pp. 22607–22613.

Kickhoefer, V. et al. Vaults Are Up–regulated in Multi-drug–resistant Cancer Cell Lines. J. Biol. Chem., Apr. 10, 1998, vol. 273, No. 15, pp. 8971–8974.

Bork, Peer et al. A superfamily of conserved domains in DNA damage–responsive cell–cycle checkpoint proteins. The Faseb J. 11:68–76, 1997.

Callebaut, Isabelle et al. From BRCA1 to RAP1: a widespread BRCT module closely associated with DNA repair. FEBS Letter 400:25–30, 1997.

Golemis, Erica A. et al. Interaction Trap/Two–Hybrid System to Identify Interacting Proteins. *Current Protocols in Mol. Biol.* 20.1.1–20.35 John Willey & Sons, 1997.

Hart, S.M. et al., "Expression of the human major vault protein LRP in acute myeloid leukemia," *Experimental Hematology*, 25(12):1227–1232, Nov. 1997.

Inman, E.M. et al., "Targeted Degradation of the Vault RNA (vRNA) in vivo Using Antisense Oligodeoxynucleotides," *Molecular Biology of the Cell*, vol. 6, Suppl., p. 196a.

Izquierdo, M.A. et al., "Relationship of LRP–human major vault protein to in vitro and clinical resisttance to anticancer drugs," *Cytotechnology*, 19(3):191–197, 1996.

Kickhoefer, V.A. et al., "Multidrug resistant cancer cell lines contain elevated levels of vaults," *Proceedings of the American Association for Cancer Research Annual Meeting*, 38:252, 1997.

Kickhoefer, V.A. et al., "Vault Ribonucleoprotein Particles from Rat and Bullfrog Contain Related Small RNA That Is Transcribed by RNA Ploymerase III," *The Journal of Biological Chemistry*, 268(11):7868–7873, Apr. 15, 1993.

"Bio–Critical Synergy: The Biotechnology Industry and IP Protection" pp. 75, 100–107, Presented Oct. 17, 1994, San Diego, CA Nagase, DNA Res 17:17–24, 1996.

*Primary Examiner*—Nancy A. Johnson
*Attorney, Agent, or Firm*—Daivd A. Farah; Sheldon & Mak

[57] ABSTRACT

A protein consisting essentially of purified human minor vault protein p193 or purified biologically active variants thereof, or a combination of purified human minor vault protein p193 and biologically active variants thereof. Also, a polynucleotide molecule encoding a protein which consists essentially of human minor vault protein p193, or its complementary strands. Further, there is provided a method of diagnosing and a method of treating patients with multidrug resistant cancer.

14 Claims, 10 Drawing Sheets

```
CCAAGGCCCTGTGCCTGGCACTTGTGCTGACTGGATCCCACAGTCGGGTCTCTTGTCCCACAGGACCTCCCAGAACCCACCTTCTGCACCCTATTGTGGC   4300
GGTTCCGGGACACGGACCGTGAACACGACTGACCTAGGGTGTCAGCCCGCAGAACAGGGTGTCCTGGAGGGGTCTTGGGTGGAAGACGTGGGATAACACCG

ATTGTTTTTCAGGGAGCTCATTAAGTCTCTGCACAGTCTGCTCACTGCAACATCCTGGAGGCTTACTACCAGGCCTTCTCTGCTGGCACCTTCCCTGAGC   4400
TAACAAAAGTCCCTCGAGTAATTCGAGACGTGTCAGAGACTGAGTTGTAGGACCTCCGAAATGATGGTCCGGAAGACGACCGTGGAAGGGACTCG

TGGATTCTCCCCAGCTTCATTTCTCTTCCTACAGACCCTGATCCCATCAGAGGTTTTGGGTCTCTTATCATCCCTCTGCTTACTCTCCTTTTCATTTTCA   4500
ACCTAAGAGGGGTCGAAGTAAAGAGAAGGATGTCTGGGACTAGGTAGTCTCCAAAACCCAGAATACTAGGGAGACGAATGAGAGGAAAAGTAAAAGT

ACCTTCCGGCAGCCTCTTTGACTGCCAACCTTAGGCTGCCAATGGCCTCTGAGGCTCTTTGCCAGTCAGTCCCCGGACTACCCCAGTAGATCTC   4600
TGGAAGGCGTCGGAGAAACTGACGGTTGGAATCCGACGGTTACCGGAGAAGTCAGTCAGTCAGAGAAAGTCAGTTCAGGGCCTGATGGGGTCATCTAGAG

TGTCTTCTAGAAGAATCAGTAGGCAGTCTCGAAGGAAGTCGATGTCCTGTTTGCTCTTTCAAAGTTCTGACACAGAAAGTGATGAGCTATCAGAAGTAC   4700
ACAGAAGATCTTCTTAGTCATCCGTCAGAGCTTCCTTCCAGCTACAGGACAGAAACGAAAAGTTCAAGACTGTGTCTTCACTACTCGATAGTCTTCATG

TTCAAGACAGCTGCTTTTTACAAATAAAGTGTGATACAAAAGATGACAGTATCCCGTGCTTTCTGGAATTAAAAGAAGAGGATGAAATAGTGTGCACACA   4800
AAGTTCTGTCGACGAAAAATGTTTATTTCACACTATGTTTTTCTACTGTCATAGGGCACGAAAGACCTTAATTTCTTCTCCTACTTTATCACACGTGTGT
```

FIG. 1i

```
ACACTGGCAGGATGCTGTGCCTTGGACAGAACTCCTCAGTCTCTCAGACTACAGAGGCTTCTGGAAACTTACACCAGAACTGGACTTATATTAAATCTT
                                                                                                    4900
TGTGACCGTCCTACGACACGGAACCTGTCTGTCTGTCTGTTGAGGAGTCAGAGTCTGTTCCTACCGAAGACCTTTGAATGTGGTCTTGACCCTGAATATAATTTAGAA

AATACAAATGGTTTGCACAGCTTTCTCTTAAACAAAAAGGCATTCAATCTCTAGGTGTAAAGGAAGAGAATGTCTCCTGGACCTAATTGCCACAATGCTGG
                                                                                                    5000
TTATGTTTACCAAACGTGTCGAAAGAATTTGTTTTTCCGTAAGTTAGAGATCCACACATTTCCCTTACAGAGGACCTGGATTAACGGTGTTACGACC

TACTACAGTTTATTCGCACCAGGTTGGAAAAAGAGGGAATAGTGTTCAAATCACTGATGAAAATGGATGACCCTTCTATTTCCAGGAATATTCCCTGGGC
                                                                                                    5100
ATGATGTCAAATAAGCGTGGTCCAACCTTTTCTCCCTTATCACAAGTTTAGTGACTACTTTACCTGGAAGATAAGGTCCTTATAAGGGACCCG

TTTTGAGGCAATAAAGCAAGTGAATGGGTAAGAAGAACTGAACTTCTTCTTGACTTCCTGTCCCCTCTTCATAGAGTCCTCCATTACAGTCAAGTCAAGG
                                                                                                    5200
AAAACTCCGTTATTTCGTTCGTTCACTTACCCATTCTTCTTGACTTGAAGAAGAACTGAAGGACACAGGGTGCCAACTTGACCCTTGCTGACCCTGAGA

GCCACCAAGCAGTTGCTGGGACTCCAGCTCCAGCCCATAAGCAGCCCATAAGATCAAATGATAATAGATAATTATAATTATAATTCATTAAGGTTTCATTCAGTGTAGCAATTAAGTT
                                                                                                    5300
CGGTGGTTCGTCAACGACCCTGAGGTCGGGTATTCGGAAGAAGTATCTCAGGAGGTAATGTCAGTTCCGATTCAGTTTACTTTGACTTAAA

TAAAACTTTTTGCATGCTTCCTATGTAGAAAATCTTTATTTAGTTACTATTCTATTAATTACTTGAGTAATCCAAAGTAAGTCACATCGTTAATGACAGA
                                                                                                    5400
ATTTGAAAACGTACGAAGATACATCTTTAGTTATTAGAATATTACTTATTAATTACTTGAGTAAGTTCATTTGAATACTTTT

TTAAAAATTAAGTGGAAGAAGAATTACTTTAATCAACTAACAAGCAATAATTAAATAAAATAAAAAAAAAAAAAAAAAA
                                                                                   ↑ 5490
AATTTTTAATTCACCTTCTTCTTCTTAATGAAATTAGTTGATTGTTCGTTATTATTTATTTATTTATTATTATT
```

FIG. 2

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 5490 base pairs
      (B) TYPE: nucleic acid
      (C) STRANDEDNESS: double stranded
      (D) TOPOLOGY: linear (ii) MOLECULE TYPE: cDNA (ix) SEQUENCE DESCRIPTION: SEQ ID NO:1:

```
CGCCCGCCCA GCCCCGGGGG CAGGGAAAGC CTAAATTACG GAATTACCGC GAGCAAGGAG         60

CGCGGAATCG GGGAGCGTCC GGAGCTAGCT GGATCCTCTA GGCAGG ATG GTG ATG          115
                                                 Met Val Met
                                                  1
```

```
GGA ATC TTT GCA AAT TGT ATC TTC TGT TTG AAA GTG AAG TAC TTA CCT      163
Gly Ile Phe Ala Asn Cys Ile Phe Cys Leu Lys Val Lys Tyr Leu Pro
          5                  10                  15

CAG CAG CAG AAG AAA AAG CTA CAA ACT GAC ATT AAG GAA AAT GGC GGA      211
Gln Gln Gln Lys Lys Lys Leu Gln Thr Asp Ile Lys Glu Asn Gly Gly
 20                  25                  30                  35

AAG TTT TCC TTT TCG TTA AAT CCT CAG TGC ACA CAT ATA ATC TTA GAT      259
Lys Phe Ser Phe Ser Leu Asn Pro Gln Cys Thr His Ile Ile Leu Asp
                 40                  45                  50

AAT GCT GAT GTT CTG AGT CAG TAC CAA CTG AAT TCT ATC CAA AAG AAC      307
Asn Ala Asp Val Leu Ser Gln Tyr Gln Leu Asn Ser Ile Gln Lys Asn
             55                  60                  65

CAC GTT CAT ATT GCA AAC CCA GAT TTT ATA TGG AAA TCT ATC AGA GAA      355
His Val His Ile Ala Asn Pro Asp Phe Ile Trp Lys Ser Ile Arg Glu
         70                  75                  80

AAG AGA CTC TTG GAT GTA AAG AAT TAT GAT CCT TAT AAG CCC CTG GAC      403
Lys Arg Leu Leu Asp Val Lys Asn Tyr Asp Pro Tyr Lys Pro Leu Asp
 85                  90                  95

ATC ACA CCA CCT CCT GAT CAG AAG GCG AGC AGT TCT GAA GTG AAA ACA      451
Ile Thr Pro Pro Pro Asp Gln Lys Ala Ser Ser Ser Glu Val Lys Thr
100                 105                 110                 115

GAA GGT CTA TGC CCG GAC AGT GCC ACA GAG GAG GAA GAC ACT GTG GAA      499
Glu Gly Leu Cys Pro Asp Ser Ala Thr Glu Glu Glu Asp Thr Val Glu
                120                 125                 130

CTC ACT GAG TTT GGT ATG CAG AAT GTT GAA ATT CCT CAT CTT CCT CAA      547
Leu Thr Glu Phe Gly Met Gln Asn Val Glu Ile Pro His Leu Pro Gln
            135                 140                 145

GAT TTT GAA GTT GCA AAA TAT AAC ACC TTG GAG AAA GTG GGA ATG GAG      595
Asp Phe Glu Val Ala Lys Tyr Asn Thr Leu Glu Lys Val Gly Met Glu
        150                 155                 160

GGA GGC CAG GAA GCT GTG GTG GTG GAG CTT CAG TGT TCG CGG GAC TCC      643
Gly Gly Gln Glu Ala Val Val Val Glu Leu Gln Cys Ser Arg Asp Ser
    165                 170                 175

AGG GAC TGT CCT TTC CTG ATA TCC TCA CAC TTC CTC CTG GAT GAT GGC      691
Arg Asp Cys Pro Phe Leu Ile Ser Ser His Phe Leu Leu Asp Asp Gly
180                 185                 190                 195

ATG GAG ACT AGA AGA CAG TTT GCT ATA AAG AAA ACC TCT GAA GAT GCA      739
Met Glu Thr Arg Arg Gln Phe Ala Ile Lys Lys Thr Ser Glu Asp Ala
                200                 205                 210

AGT GAA TAC TTT GAA AAT TAC ATT GAA GAA CTG AAG AAA CAA GGA TTT      787
Ser Glu Tyr Phe Glu Asn Tyr Ile Glu Glu Leu Lys Lys Gln Gly Phe
            215                 220                 225

CTA CTA AGA GAA CAT TTC ACA CCT GAA GCA ACC CAA TTA GCA TCT GAA      835
Leu Leu Arg Glu His Phe Thr Pro Glu Ala Thr Gln Leu Ala Ser Glu
        230                 235                 240

CAA TTG CAA GCA TTG CTT TTG GAG GAA GTC ATG AAT TCA AGC ACT CTG      883
Gln Leu Gln Ala Leu Leu Leu Glu Glu Val Met Asn Ser Ser Thr Leu
    245                 250                 255

AGC CAA GAG GTG AGC GAT TTA GTA GAG ATG ATT TGG GCA GAG GCC CTG      931
Ser Gln Glu Val Ser Asp Leu Val Glu Met Ile Trp Ala Glu Ala Leu
260                 265                 270                 275

GGC CAC CTG GAA CAC ATG CTT CTC AAG CCA GTG AAC AGG ATT AGC CTC      979
Gly His Leu Glu His Met Leu Leu Lys Pro Val Asn Arg Ile Ser Leu
                280                 285                 290

AAC GAT GTG AGC AAG GCA GAG GGG ATT CTC CTT CTA GTA AAG GCA GCA     1027
Asn Asp Val Ser Lys Ala Glu Gly Ile Leu Leu Leu Val Lys Ala Ala
            295                 300                 305
```

-continued

```
CTG AAA AAT GGA GAA ACA GCA GAG CAA TTG CAA AAG ATG ATG ACA GAG    1075
Leu Lys Asn Gly Glu Thr Ala Glu Gln Leu Gln Lys Met Met Thr Glu
        310                 315                 320

TTT TAC AGA CTG ATA CCT CAC AAA GGC ACA ATG CCC AAA GAA GTG AAC    1123
Phe Tyr Arg Leu Ile Pro His Lys Gly Thr Met Pro Lys Glu Val Asn
    325                 330                 335

CTG GGA CTA TTG GCT AAG AAA GCA GAC CTC TGC CAG CTA ATA AGA GAC    1171
Leu Gly Leu Leu Ala Lys Lys Ala Asp Leu Cys Gln Leu Ile Arg Asp
340                 345                 350                 355

ATG GTT AAT GTC TGT GAA ACT AAT TTG TCC AAA CCC AAC CCA CCA TCC    1219
Met Val Asn Val Cys Glu Thr Asn Leu Ser Lys Pro Asn Pro Pro Ser
                360                 365                 370

CTG GCC AAA TAC CGA GCT TTG AGG TGC AAA ATT GAG CAT GTT GAA CAG    1267
Leu Ala Lys Tyr Arg Ala Leu Arg Cys Lys Ile Glu His Val Glu Gln
            375                 380                 385

AAT ACT GAA GAA TTT CTC AGG GTT AGA AAA GAG GTT TTG CAG AAT CAT    1315
Asn Thr Glu Glu Phe Leu Arg Val Arg Lys Glu Val Leu Gln Asn His
        390                 395                 400

CAC AGT AAG AGC CCA GTG GAT GTC TTG CAG ATA TTT AGA GTT GGC AGA    1363
His Ser Lys Ser Pro Val Asp Val Leu Gln Ile Phe Arg Val Gly Arg
    405                 410                 415

GTG AAT GAA ACC ACA GAG TTT TTG AGC AAA CTT GGT AAT GTG AGG CCC    1411
Val Asn Glu Thr Thr Glu Phe Leu Ser Lys Leu Gly Asn Val Arg Pro
420                 425                 430                 435

TTG TTG CAT GGT TCT CCT GTA CAA AAC ATC GTG GGA ATC TTG TGT CGA    1459
Leu Leu His Gly Ser Pro Val Gln Asn Ile Val Gly Ile Leu Cys Arg
                440                 445                 450

GGG TTG CTT TTA CCC AAA GTA GTG GAA GAT CGT GGT GTG CAA AGA ACA    1507
Gly Leu Leu Leu Pro Lys Val Val Glu Asp Arg Gly Val Gln Arg Thr
            455                 460                 465

GAC GTC GGA AAC CTT GGA AGT GGG ATT TAT TTC AGT GAT TCG CTC AGT    1555
Asp Val Gly Asn Leu Gly Ser Gly Ile Tyr Phe Ser Asp Ser Leu Ser
        470                 475                 480

ACA AGT ATC AAG TAC TCA CAC CCG GGA GAG ACA GAT GGC ACC AGA CTC    1603
Thr Ser Ile Lys Tyr Ser His Pro Gly Glu Thr Asp Gly Thr Arg Leu
    485                 490                 495

CTG CTC ATT TGT GAC GTA GCC CTC GGA AAG TGT ATG GAC TTA CAT GAG    1651
Leu Leu Ile Cys Asp Val Ala Leu Gly Lys Cys Met Asp Leu His Glu
500                 505                 510                 515

AAG GAC TTT CCC TTA ACT GAA GCA CCA CCA GGC TAC GAC AGT GTG CAT    1699
Lys Asp Phe Pro Leu Thr Glu Ala Pro Pro Gly Tyr Asp Ser Val His
                520                 525                 530

GGA GTT TCA CAA ACA GCC TCT GTC ACC ACA GAC TTT GAG GAT GAT GAA    1747
Gly Val Ser Gln Thr Ala Ser Val Thr Thr Asp Phe Glu Asp Asp Glu
            535                 540                 545

TTT GTT GTC TAT AAA ACC AAT CAG GTT AAA ATG AAA TAT ATT ATT AAA    1795
Phe Val Val Tyr Lys Thr Asn Gln Val Lys Met Lys Tyr Ile Ile Lys
        550                 555                 560

TTT TCC ATG CCT GGA GAT CAG ATA AAG GAC TTT CAT CCT AGT GAT CAT    1843
Phe Ser Met Pro Gly Asp Gln Ile Lys Asp Phe His Pro Ser Asp His
    565                 570                 575

ACT GAA TTA GAG GAA TAC AGA CCT GAG TTT TCA AAT TTT TCA AAG GTT    1891
Thr Glu Leu Glu Glu Tyr Arg Pro Glu Phe Ser Asn Phe Ser Lys Val
580                 585                 590                 595

GAA GAT TAC CAG TTA CCA GAT GCC AAA ACT TCC AGC AGC ACC AAG GCC    1939
Glu Asp Tyr Gln Leu Pro Asp Ala Lys Thr Ser Ser Ser Thr Lys Ala
                600                 605                 610

GGC CTC CAG GAT GCC TCT GGG AAC TTG GTT CCT CTG GAG GAT GTC CAC    1987
Gly Leu Gln Asp Ala Ser Gly Asn Leu Val Pro Leu Glu Asp Val His
            615                 620                 625
```

```
ATC AAA GGG AGA ATC ATA GAC ACT GTA GCC CAG GTC ATT GTT TTT CAG    2035
Ile Lys Gly Arg Ile Ile Asp Thr Val Ala Gln Val Ile Val Phe Gln
            630                 635                 640

ACA TAC ACA AAT AAA AGT CAC GTG CCC ATT GAG GCA AAA TAT ATC TTT    2083
Thr Tyr Thr Asn Lys Ser His Val Pro Ile Glu Ala Lys Tyr Ile Phe
            645                 650                 655

CCT TTG GAT GAC AAG GCC GCT GTG TGT GGC TTC GAA GCC TTC ATC AAT    2131
Pro Leu Asp Asp Lys Ala Ala Val Cys Gly Phe Glu Ala Phe Ile Asn
660                 665                 670                 675

GGG AAG CAC ATA GTT GGA GAG ATT AAA GAG AAG GAA GAA GCC CAG CAA    2179
Gly Lys His Ile Val Gly Glu Ile Lys Glu Lys Glu Glu Ala Gln Gln
                680                 685                 690

GAG TAC CTA GAA GCC GTG ACC CAG GGC CAT GGC GCT TAC CTG ATG AGT    2227
Glu Tyr Leu Glu Ala Val Thr Gln Gly His Gly Ala Tyr Leu Met Ser
            695                 700                 705

CAG GAT GCT CCG GAC GTT TTT ACT GTA AGT GTT GGA AAC TTA CCC CCT    2275
Gln Asp Ala Pro Asp Val Phe Thr Val Ser Val Gly Asn Leu Pro Pro
            710                 715                 720

AAG GCT AAG GTT CTT ATA AAA ATT ACC TAC ATC ACA GAA CTC AGC ATC    2323
Lys Ala Lys Val Leu Ile Lys Ile Thr Tyr Ile Thr Glu Leu Ser Ile
725                 730                 735

CTG GGC ACT GTT GGT GTC TTT TTC ATG CCC GCC ACC GTA GCA CCC TGG    2371
Leu Gly Thr Val Gly Val Phe Phe Met Pro Ala Thr Val Ala Pro Trp
740                 745                 750                 755

CAA CAG GAC AAG GCT TTG AAT GAA AAC CTT CAG GAT ACA GTA GAG AAG    2419
Gln Gln Asp Lys Ala Leu Asn Glu Asn Leu Gln Asp Thr Val Glu Lys
            760                 765                 770

ATT TGT ATA AAA GAA ATA GGA ACA AAG CAA AGC TTC TCT TTG ACT ATG    2467
Ile Cys Ile Lys Glu Ile Gly Thr Lys Gln Ser Phe Ser Leu Thr Met
            775                 780                 785

TCT ATT GAG ATG CCG TAT GTG ATT GAA TTC ATT TTC AGT GAT ACA CAT    2515
Ser Ile Glu Met Pro Tyr Val Ile Glu Phe Ile Phe Ser Asp Thr His
            790                 795                 800

GAA CTG AAA CAA AAG CGC ACA GAC TGC AAA GCT GTC ATT AGC ACC ATG    2563
Glu Leu Lys Gln Lys Arg Thr Asp Cys Lys Ala Val Ile Ser Thr Met
805                 810                 815

GAA GGC AGC TCC TTA GAC AGC AGT GGA TTT TCT CTC CAC ATC GGT TTG    2611
Glu Gly Ser Ser Leu Asp Ser Ser Gly Phe Ser Leu His Ile Gly Leu
820                 825                 830                 835

TCT GCT GCC TAT CTC CCA AGA ATG TGG GTT GAA AAA CAT CCA GAA AAA    2659
Ser Ala Ala Tyr Leu Pro Arg Met Trp Val Glu Lys His Pro Glu Lys
            840                 845                 850

GAA AGC GAG GCT TGC ATG CTT GTC TTT CAA CCC GAT CTC GAT GTC GAC    2707
Glu Ser Glu Ala Cys Met Leu Val Phe Gln Pro Asp Leu Asp Val Asp
            855                 860                 865

CTC CCT GAC CTA GCC AGT GAG AGC GAA GTG ATT ATT TGT CTT GAC TGC    2755
Leu Pro Asp Leu Ala Ser Glu Ser Glu Val Ile Ile Cys Leu Asp Cys
            870                 875                 880

TCC AGT TCC ATG GAG GGT GTG ACA TTC TTG CAA GCC AAG CAA ATC ACC    2803
Ser Ser Ser Met Glu Gly Val Thr Phe Leu Gln Ala Lys Gln Ile Thr
            885                 890                 895

TTG CAT GCG CTG TCC TTG GTG GGT GAG AAG CAG AAA GTA AAT ATT ATC    2851
Leu His Ala Leu Ser Leu Val Gly Glu Lys Gln Lys Val Asn Ile Ile
900                 905                 910                 915

CAG TTC GGC ACA GGT TAC AAG GAG CTA TTT TCG TAT CCT AAG CAT ATC    2899
Gln Phe Gly Thr Gly Tyr Lys Glu Leu Phe Ser Tyr Pro Lys His Ile
            920                 925                 930
```

-continued

| | |
|---|---|
| ACA AGC AAT ACC ACG GCA GCA GAG TTC ATC ATG TCT GCC ACA CCT ACC<br>Thr Ser Asn Thr Thr Ala Ala Glu Phe Ile Met Ser Ala Thr Pro Thr<br>             935                         940                         945 | 2947 |
| ATG GGG AAC ACA GAC TTC TGG AAA ACA CTC CGA TAT CTT AGC TTA TTG<br>Met Gly Asn Thr Asp Phe Trp Lys Thr Leu Arg Tyr Leu Ser Leu Leu<br>         950                          955                         960 | 2995 |
| TAC CCT GCT CGA GGG TCA CGG AAC ATC CTC CTG GTG TCT GAT GGG CAC<br>Tyr Pro Ala Arg Gly Ser Arg Asn Ile Leu Leu Val Ser Asp Gly His<br>         965                          970                         975 | 3043 |
| CTC CAG GAT GAG AGC CTG ACA TTA CAG CTC GTG AAG AGG AGC CGC CCG<br>Leu Gln Asp Glu Ser Leu Thr Leu Gln Leu Val Lys Arg Ser Arg Pro<br>980                         985                         990                         995 | 3091 |
| CAC ACC AGG TTA TTC GCC TGC GGT ATC GGT TCT ACA GCA AAT CGT CAC<br>His Thr Arg Leu Phe Ala Cys Gly Ile Gly Ser Thr Ala Asn Arg His<br>                         1000                     1005                     1010 | 3139 |
| GTC TTA AGG ATT TTG TCC CAG TGT GGT GCC GGA GTA TTT GAA TAT TTT<br>Val Leu Arg Ile Leu Ser Gln Cys Gly Ala Gly Val Phe Glu Tyr Phe<br>             1015                     1020                      1025 | 3187 |
| AAT GCA AAA TCC AAG CAT AGT TGG AGA AAA CAG ATA GAA GAC CAA ATG<br>Asn Ala Lys Ser Lys His Ser Trp Arg Lys Gln Ile Glu Asp Gln Met<br>             1030                     1035                      1040 | 3235 |
| ACC AGG CTA TGT TCT CCG AGT TGC CAC TCT GTC TCC GTC AAA TGG CAG<br>Thr Arg Leu Cys Ser Pro Ser Cys His Ser Val Ser Val Lys Trp Gln<br>             1045                     1050                      1055 | 3283 |
| CAA CTC AAT CCA GAT GCG CCC GAG GCC CTG CAG GCC CCA GCC CAG GTG<br>Gln Leu Asn Pro Asp Ala Pro Glu Ala Leu Gln Ala Pro Ala Gln Val<br>1060                   1065                     1070                      1075 | 3331 |
| CCA TCC TTG TTT CGC AAT GAT CGA CTC CTT GTC TAT GGA TTC ATT CCT<br>Pro Ser Leu Phe Arg Asn Asp Arg Leu Leu Val Tyr Gly Phe Ile Pro<br>                   1080                     1085                     1090 | 3379 |
| CAC TGC ACA CAA GCA ACT CTG TGT GCA CTA ATT CAA GAG AAA GAA TTT<br>His Cys Thr Gln Ala Thr Leu Cys Ala Leu Ile Gln Glu Lys Glu Phe<br>             1095                     1100                      1105 | 3427 |
| TGT ACA ATG GTG TCG ACT ACT GAG CTT CAG AAG ACA ACT GGA ACT ATG<br>Cys Thr Met Val Ser Thr Thr Glu Leu Gln Lys Thr Thr Gly Thr Met<br>             1110                     1115                      1120 | 3475 |
| ATC CAC AAG CTG GCA GCC CGA GCT CTA ATC AGA GAT TAT GAA GAT GGC<br>Ile His Lys Leu Ala Ala Arg Ala Leu Ile Arg Asp Tyr Glu Asp Gly<br>             1125                     1130                      1135 | 3523 |
| ATT CTT CAC GAA AAT GAA ACC AGT CAT GAG ATG AAA AAA CAA ACC TTG<br>Ile Leu His Glu Asn Glu Thr Ser His Glu Met Lys Lys Gln Thr Leu<br>1140                   1145                     1150                      1155 | 3571 |
| AAA TCT CTG ATT ATT AAA CTC AGT AAA GAA AAC TCT CTC ATA ACA CAA<br>Lys Ser Leu Ile Ile Lys Leu Ser Lys Glu Asn Ser Leu Ile Thr Gln<br>             1160                     1165                      1170 | 3619 |
| TTT ACA AGC TTT GTG GCA GTT GAG AAA AGG GAT GAG AAT GAG TCG CCT<br>Phe Thr Ser Phe Val Ala Val Glu Lys Arg Asp Glu Asn Glu Ser Pro<br>             1175                     1180                      1185 | 3667 |
| TTT CCT GAT ATT CCA AAA GTT TCT GAA CTT ATT GCC AAA GAA GAT GTA<br>Phe Pro Asp Ile Pro Lys Val Ser Glu Leu Ile Ala Lys Glu Asp Val<br>             1190                     1195                      1200 | 3715 |
| GAC TTC CTG CCC TAC ATG AGC TGG CAG GGG GAG CCC CAA GAA GCC GTC<br>Asp Phe Leu Pro Tyr Met Ser Trp Gln Gly Glu Pro Gln Glu Ala Val<br>         1205                         1210                     1215 | 3763 |
| AGG AAC CAG TCT CTT TTA GCA TCC TCT GAG TGG CCA GAA TTA CGT TTA<br>Arg Asn Gln Ser Leu Leu Ala Ser Ser Glu Trp Pro Glu Leu Arg Leu<br>1220                   1225                     1230                      1235 | 3811 |
| TCC AAA CGA AAA CAT AGG AAA ATT CCA TTT TCC AAA AGA AAA ATG GAA<br>Ser Lys Arg Lys His Arg Lys Ile Pro Phe Ser Lys Arg Lys Met Glu<br>             1240                     1245                      1250 | 3859 |

-continued

| | |
|---|---|
| TTA TCT CAG CCA GAA GTT TCT GAA GAT TTT GAA GAG GAT GGC TTA GGT<br>Leu Ser Gln Pro Glu Val Ser Glu Asp Phe Glu Glu Asp Gly Leu Gly<br>                1255                          1260                    1265 | 3907 |
| GTA CTA CCA GCT TTC ACA TCA AAT TTG GAA CGT GGA GGT GTG GAA AAG<br>Val Leu Pro Ala Phe Thr Ser Asn Leu Glu Arg Gly Gly Val Glu Lys<br>      1270                     1275                    1280 | 3955 |
| CTA TTG GAT TTA AGT TGG ACA GAG TCA TGT AAA CCA ACA GCA ACT GAA<br>Leu Leu Asp Leu Ser Trp Thr Glu Ser Cys Lys Pro Thr Ala Thr Glu<br>1285                    1290                    1295 | 4003 |
| CCA CTA TTT AAG AAA GTC AGT CCA TGG GAA ACA TCT ACT TCT AGC TTT<br>Pro Leu Phe Lys Lys Val Ser Pro Trp Glu Thr Ser Thr Ser Ser Phe<br>1300                    1305                  1310                1315 | 4051 |
| TTT CCT ATT TTG GCT CCG GCC GTT GGT TCC TAT CTT ACC CCG ACT ACC<br>Phe Pro Ile Leu Ala Pro Ala Val Gly Ser Tyr Leu Thr Pro Thr Thr<br>                1320                    1325                    1330 | 4099 |
| CGC GCT CAC AGT CCT GCT TCC TTG TCT TTT GCC TCA TAT CGT CAG GTA<br>Arg Ala His Ser Pro Ala Ser Leu Ser Phe Ala Ser Tyr Arg Gln Val<br>                1335                    1340                    1345 | 4147 |
| GCT AGT TTC GGT TCA GCT GCT CCT CCC AGA CAG TTT GAT GCA TCT CAA<br>Ala Ser Phe Gly Ser Ala Ala Pro Pro Arg Gln Phe Asp Ala Ser Gln<br>            1350                    1355                    1360 | 4195 |
| TTC AGC CAA GGC CCT GTG CCT GGC ACT TGT GCT GAC TGG ATC CCA CAG<br>Phe Ser Gln Gly Pro Val Pro Gly Thr Cys Ala Asp Trp Ile Pro Gln<br>1365                    1370                    1375 | 4243 |
| TCG GCG TCT TGT CCC ACA GGA CCT CCC CAG AAC CCA CCT TCT GCA CCC<br>Ser Ala Ser Cys Pro Thr Gly Pro Pro Gln Asn Pro Pro Ser Ala Pro<br>1380                    1385                    1390                    1395 | 4291 |
| TAT TGT GGC ATT GTT TTT TCA GGG AGC TCA TTA AGC TCT GCA CAG TCT<br>Tyr Cys Gly Ile Val Phe Ser Gly Ser Ser Leu Ser Ser Ala Gln Ser<br>                1400                    1405                    1410 | 4339 |
| GCT CCA CTG CAA CAT CCT GGA GGC TTT ACT ACC AGG CCT TCT GCT GGC<br>Ala Pro Leu Gln His Pro Gly Gly Phe Thr Thr Arg Pro Ser Ala Gly<br>            1415                    1420                    1425 | 4387 |
| ACC TTC CCT GAG CTG GAT TCT CCC CAG CTT CAT TTC TCT CTT CCT ACA<br>Thr Phe Pro Glu Leu Asp Ser Pro Gln Leu His Phe Ser Leu Pro Thr<br>                1430                    1435                    1440 | 4435 |
| GAC CCT GAT CCC ATC AGA GGT TTT GGG TCT TAT CAT CCC TCT GCT TAC<br>Asp Pro Asp Pro Ile Arg Gly Phe Gly Ser Tyr His Pro Ser Ala Tyr<br>            1445                    1450                    1455 | 4483 |
| TCT CCT TTT CAT TTT CAA CCT TCC GCA GCC TCT TTG ACT GCC AAC CTT<br>Ser Pro Phe His Phe Gln Pro Ser Ala Ala Ser Leu Thr Ala Asn Leu<br>1460                    1465                    1470                    1475 | 4531 |
| AGG CTG CCA ATG GCC TCT GCT TTA CCT GAG GCT CTT TGC AGT CAG TCC<br>Arg Leu Pro Met Ala Ser Ala Leu Pro Glu Ala Leu Cys Ser Gln Ser<br>                1480                    1485                    1490 | 4579 |
| CGG ACT ACC CCA GTA GAT CTC TGT CTT CTA GAA GAA TCA GTA GGC AGT<br>Arg Thr Thr Pro Val Asp Leu Cys Leu Leu Glu Glu Ser Val Gly Ser<br>            1495                    1500                    1505 | 4627 |
| CTC GAA GGA AGT CGA TGT CCT GTC TTT GCT TTT CAA AGT TCT GAC ACA<br>Leu Glu Gly Ser Arg Cys Pro Val Phe Ala Phe Gln Ser Ser Asp Thr<br>                1510                    1515                    1520 | 4675 |
| GAA AGT GAT GAG CTA TCA GAA GTA CTT CAA GAC AGC TGC TTT TTA CAA<br>Glu Ser Asp Glu Leu Ser Glu Val Leu Gln Asp Ser Cys Phe Leu Gln<br>1525                    1530                    1535 | 4723 |
| ATA AAG TGT GAT ACA AAA GAT GAC AGT ATC CCG TGC TTT CTG GAA TTA<br>Ile Lys Cys Asp Thr Lys Asp Asp Ser Ile Pro Cys Phe Leu Glu Leu<br>1540                    1545                    1550                    1555 | 4771 |

-continued

```
AAA GAA GAG GAT GAA ATA GTG TGC ACA CAA CAC TGG CAG GAT GCT GTG      4819
Lys Glu Glu Asp Glu Ile Val Cys Thr Gln His Trp Gln Asp Ala Val
                1560                1565                1570

CCT TGG ACA GAA CTC CTC AGT CTA CAG ACA GAG GAT GGC TTC TGG AAA      4867
Pro Trp Thr Glu Leu Leu Ser Leu Gln Thr Glu Asp Gly Phe Trp Lys
            1575                1580                1585

CTT ACA CCA GAA CTG GGA CTT ATA TTA AAT CTT AAT ACA AAT GGT TTG      4915
Leu Thr Pro Glu Leu Gly Leu Ile Leu Asn Leu Asn Thr Asn Gly Leu
        1590                1595                1600

CAC AGC TTT CTT AAA CAA AAA GGC ATT CAA TCT CTA GGT GTA AAA GGA      4963
His Ser Phe Leu Lys Gln Lys Gly Ile Gln Ser Leu Gly Val Lys Gly
    1605                1610                1615

AGA GAA TGT CTC CTG GAC CTA ATT GCC ACA ATG CTG GTA CTA CAG TTT      5011
Arg Glu Cys Leu Leu Asp Leu Ile Ala Thr Met Leu Val Leu Gln Phe
1620                1625                1630                1635

ATT CGC ACC AGG TTG GAA AAA GAG GGA ATA GTG TTC AAA TCA CTG ATG      5059
Ile Arg Thr Arg Leu Glu Lys Glu Gly Ile Val Phe Lys Ser Leu Met
                1640                1645                1650

AAA ATG GAT GAC CCT TCT ATT TCC AGG AAT ATT CCC TGG GCT TTT GAG      5107
Lys Met Asp Asp Pro Ser Ile Ser Arg Asn Ile Pro Trp Ala Phe Glu
            1655                1660                1665

GCA ATA AAG CAA GCA AGT GAA TGG GTA AGA AGA ACT GAA GGA CAG TAC      5155
Ala Ile Lys Gln Ala Ser Glu Trp Val Arg Arg Thr Glu Gly Gln Tyr
        1670                1675                1680

CCA TCT ATC TGC CCA CGG CTT GAA CTG GGG AAC GAC TGG GAC TCT GCC      5203
Pro Ser Ile Cys Pro Arg Leu Glu Leu Gly Asn Asp Trp Asp Ser Ala
    1685                1690                1695

ACC AAG CAG TTG CTG GGA CTC CAG CCC ATA AGC ACT GTG TCC CCT CTT      5251
Thr Lys Gln Leu Leu Gly Leu Gln Pro Ile Ser Thr Val Ser Pro Leu
1700                1705                1710                1715

CAT AGA GTC CTC CAT TAC AGT CAA GGC TAAGTCAAAT GAAACTGAAT TTTAA      5303
His Arg Val Leu His Tyr Ser Gln Gly
                1720

ACTTTTTGCA TGCTTCTATG TAGAAAATAA TCAAATGATA ATAGATAATT ATAATGAAAC    5363

TTCATTAAGG TTTCATTCAG TGTAGCAATT ACTGTCTTTA AAAATTAAGT GGAAGAAGAA    5423

TTACTTTAAT CAACTAACAA GCAATAATAA AATGAAACTT AAAATAAAAA AAAAAAAAA     5483

AAAAAAA                                                              5490

(2) INFORMATION FOR SEQ ID NO:2:

(i) SEQUENCE CHARACTERISTICS:
        (A) LENGTH: 1724 amino acids
        (B) TYPE: amino acid
        (C) TOPOLOGY: linear (ii) MOLECULE TYPE: protein (ix) SEQUENCE DESCRIPTION: SEQ ID NO:2:

Met Val Met Gly Ile Phe Ala Asn Cys Ile Phe Cys Leu Lys Val Lys Tyr Leu
1               5                   10                  15

Pro Gln Gln Lys Lys Leu Gln Thr Asp Ile Lys Glu Asn Gly Gly Lys
        20                  25                  30                  35

Phe Ser Phe Ser Leu Asn Pro Gln Cys Thr His Ile Ile Leu Asp Asn Ala Asp
                40                  45                  50

Val Leu Ser Gln Tyr Gln Leu Asn Ser Ile Gln Lys Asn His Val His Ile Ala
55                  60                  65                  70

Asn Pro Asp Phe Ile Trp Lys Ser Ile Arg Glu Lys Arg Leu Leu Asp Val Lys
            75                  80                  85                  90
```

-continued

```
Asn Tyr Asp Pro Tyr Lys Pro Leu Asp Ile Thr Pro Pro Asp Gln Lys Ala
             95                  100                 105

Ser Ser Ser Glu Val Lys Thr Glu Gly Leu Cys Pro Asp Ser Ala Thr Glu Glu
        110                 115                 120                 125

Glu Asp Thr Val Glu Leu Thr Glu Phe Gly Met Gln Asn Val Glu Ile Phe His
            130                 135                 140

Leu Pro Gln Asp Phe Glu Val Ala Lys Tyr Asn Thr Leu Glu Lys Val Gly Met
145                 150                 155                 160

Glu Gly Gly Gln Glu Ala Val Val Glu Leu Gln Cys Ser Arg Asp Ser Arg
            165                 170                 175                 180

Asp Cys Pro Phe Leu Ile Ser Ser His Phe Leu Asp Asp Gly Met Glu Thr
                185                 190                 195

Arg Arg Gln Phe Ala Ile Lys Lys Thr Ser Glu Asp Ala Ser Glu Tyr Phe Glu
        200                 205                 210                 215

Asn Tyr Ile Glu Glu Leu Lys Lys Gln Gly Phe Leu Leu Arg Glu His Phe Thr
            220                 225                 230

Pro Glu Ala Thr Gln Leu Ala Ser Glu Gln Leu Gln Ala Leu Leu Glu Glu
235                 240                 245                 250

Val Met Asn Ser Ser Thr Leu Ser Gln Glu Val Ser Asp Leu Val Glu Met Ile
            255                 260                 265                 270

Trp Ala Glu Ala Leu Gly His Leu Glu His Met Leu Leu Lys Pro Val Asn Arg
                275                 280                 285

Ile Ser Leu Asn Asp Val Ser Lys Ala Glu Gly Ile Leu Leu Val Lys Ala
        290                 295                 300                 305

Ala Leu Lys Asn Gly Glu Thr Ala Glu Gln Leu Gln Lys Met Met Thr Glu Phe
            310                 315                 320

Tyr Arg Leu Ile Pro His Lys Gly Thr Met Pro Lys Glu Val Asn Leu Gly Leu
325                 330                 335                 340

Leu Ala Lys Lys Ala Asp Leu Cys Gln Leu Ile Arg Asp Met Val Asn Val Cys
            345                 350                 355                 360

Glu Thr Asn Leu Ser Lys Pro Asn Pro Ser Leu Ala Lys Tyr Arg Ala Leu
            365                 370                 375

Arg Cys Lys Ile Glu His Val Glu Gln Asn Thr Glu Glu Phe Leu Arg Val Arg
        380                 385                 390                 395

Lys Glu Val Leu Gln Asn His His Ser Lys Ser Pro Val Asp Val Leu Gln Ile
            400                 405                 410

Phe Arg Val Gly Arg Val Asn Glu Thr Thr Glu Phe Leu Ser Lys Leu Gly Asn
415                 420                 425                 430

Val Arg Pro Leu Leu His Gly Ser Pro Val Gln Asn Ile Val Gly Ile Leu Cys
            435                 440                 445                 450

Arg Gly Leu Leu Leu Pro Lys Val Val Glu Asp Arg Gly Val Gln Arg Thr Asp
                455                 460                 465

Val Gly Asn Leu Gly Ser Gly Ile Tyr Phe Ser Asp Ser Leu Ser Thr Ser Ile
            470                 475                 480                 485

Lys Tyr Ser His Pro Gly Glu Thr Asp Gly Thr Arg Leu Leu Leu Ile Cys Asp
                490                 495                 500

Val Ala Leu Gly Lys Cys Met Asp Leu His Glu Lys Asp Phe Pro Leu Thr Glu
505                 510                 515                 520

Ala Pro Pro Gly Tyr Asp Ser Val His Gly Val Ser Gln Thr Ala Ser Val Thr
            525                 530                 535                 540

Thr Asp Phe Glu Asp Asp Glu Phe Val Val Tyr Lys Thr Asn Gln Val Lys Met
            545                 550                 555
```

-continued

```
Lys Tyr Ile Ile Lys Phe Ser Met Pro Gly Asp Gln Ile Lys Asp Phe His Pro
            560                 565                 570                 575

Ser Asp His Thr Glu Leu Glu Glu Tyr Arg Pro Glu Phe Ser Asn Phe Ser Lys
            580                 585                 590

Val Glu Asp Tyr Gln Leu Pro Asp Ala Lys Thr Ser Ser Thr Lys Ala Gly
595                 600                 605                 610

Leu Gln Asp Ala Ser Gly Asn Leu Val Pro Leu Glu Asp Val His Ile Lys Gly
            615                 620                 625                 630

Arg Ile Ile Asp Thr Val Ala Gln Val Ile Val Phe Gln Thr Tyr Thr Asn Lys
                    635                 640                 645

Ser His Val Pro Ile Glu Ala Lys Tyr Ile Phe Pro Leu Asp Asp Lys Ala Ala
            650                 655                 660                 665

Val Cys Gly Phe Glu Ala Phe Ile Asn Gly Lys His Ile Val Gly Glu Ile Lys
                    670                 675                 680

Glu Lys Glu Glu Ala Gln Gln Glu Tyr Leu Glu Ala Val Thr Gln Gly His Gly
685                 690                 695                 700

Ala Tyr Leu Met Ser Gln Asp Ala Pro Asp Val Phe Thr Val Ser Val Gly Asn
            705                 710                 715                 720

Leu Pro Pro Lys Ala Lys Val Leu Ile Lys Ile Thr Tyr Ile Thr Glu Leu Ser
                    725                 730                 735

Ile Leu Gly Thr Val Gly Val Phe Phe Met Pro Ala Thr Val Ala Pro Trp Gln
            740                 745                 750                 755

Gln Asp Lys Ala Leu Asn Glu Asn Leu Gln Asp Thr Val Glu Lys Ile Cys Ile
                    760                 765                 770

Lys Glu Ile Gly Thr Lys Gln Ser Phe Ser Leu Thr Met Ser Ile Glu Met Pro
775                 780                 785                 790

Tyr Val Ile Glu Phe Ile Phe Ser Asp Thr His Glu Leu Lys Gln Lys Arg Thr
            795                 800                 805                 810

Asp Cys Lys Ala Val Ile Ser Thr Met Glu Gly Ser Ser Leu Asp Ser Ser Gly
                    815                 820                 825

Phe Ser Leu His Ile Gly Leu Ser Ala Ala Tyr Leu Pro Arg Met Trp Val Glu
830                 835                 840                 845

Lys His Pro Glu Lys Glu Ser Glu Ala Cys Met Leu Val Phe Gln Pro Asp Leu
            850                 855                 860

Asp Val Asp Leu Pro Asp Leu Ala Ser Glu Ser Glu Val Ile Ile Cys Leu Asp
865                 870                 875                 880

Cys Ser Ser Ser Met Glu Gly Val Thr Phe Leu Gln Ala Lys Gln Ile Thr Leu
            885                 890                 895                 900

His Ala Leu Ser Leu Val Gly Glu Lys Gln Lys Val Asn Ile Ile Gln Phe Gly
                    905                 910                 915

Thr Gly Tyr Lys Glu Leu Phe Ser Tyr Pro Lys His Ile Thr Ser Asn Thr Thr
            920                 925                 930                 935

Ala Ala Glu Phe Ile Met Ser Thr Pro Thr Met Gly Asn Thr Asp Phe Trp
                    940                 945                 950

Lys Thr Leu Arg Tyr Leu Ser Leu Leu Tyr Pro Ala Arg Gly Ser Arg Asn Ile
955                 960                 965                 970

Leu Leu Val Ser Asp Gly His Leu Gln Asp Glu Ser Leu Thr Leu Gln Leu Val
            975                 980                 985                 990

Lys Arg Ser Arg Pro His Thr Arg Leu Phe Ala Cys Gly Ile Gly Ser Thr Ala
                    995                 1000                1005

Asn Arg His Val Leu Arg Ile Leu Ser Gln Cys Gly Ala Gly Val Phe Glu Tyr
            1010                1015                1020                1025
```

-continued

```
Phe Asn Ala Lys Ser Lys His Ser Trp Arg Lys Gln Ile Glu Asp Gln Met Thr
            1030                1035                1040

Arg Leu Cys Ser Pro Ser Cys His Ser Val Ser Val Lys Trp Gln Gln Leu Asn
1045                1050                1055                1060

Pro Asp Ala Pro Glu Ala Leu Gln Ala Pro Ala Gln Val Pro Ser Leu Phe Arg
            1065                1070                1075                1080

Asn Asp Arg Leu Leu Val Tyr Gly Phe Ile Pro His Cys Thr Gln Ala Thr Leu
                1085                1090                1095

Cys Ala Leu Ile Gln Glu Lys Glu Phe Cys Thr Met Val Ser Thr Thr Glu Leu
1100                1105                1110                1115

Gln Lys Thr Thr Gly Thr Met Ile His Lys Leu Ala Ala Arg Ala Leu Ile Arg
            1120                1125                1130

Asp Tyr Glu Asp Gly Ile Leu His Glu Asn Thr Ser His Glu Met Lys Lys
1135                1140                1145                1150

Gln Thr Leu Lys Ser Leu Ile Ile Lys Leu Ser Lys Glu Asn Ser Leu Ile Thr
            1155                1160                1165                1170

Gln Phe Thr Ser Phe Val Ala Val Glu Lys Arg Asp Glu Asn Glu Ser Pro Phe
                1175                1180                1185

Pro Asp Ile Pro Lys Val Ser Glu Leu Ile Ala Lys Glu Asp Val Asp Phe Leu
    1190                1195                1200                1205

Pro Tyr Met Ser Trp Gln Gly Glu Pro Gln Glu Ala Val Arg Asn Gln Ser Leu
    1210                1215                1220

Leu Ala Ser Ser Glu Trp Pro Glu Leu Arg Leu Ser Lys Arg Lys His Arg Lys
1225                1230                1235                1240

Ile Pro Phe Ser Lys Arg Lys Met Glu Leu Ser Gln Pro Glu Val Ser Glu Asp
            1245                1250                1255                1260

Phe Glu Glu Asp Gly Leu Gly Val Leu Pro Ala Phe Thr Ser Asn Leu Glu Arg
                1265                1270                1275

Gly Gly Val Glu Lys Leu Leu Asp Leu Ser Trp Thr Glu Ser Cys Lys Pro Thr
1280                1285                1290                1295

Ala Thr Glu Pro Leu Phe Lys Lys Val Ser Pro Trp Glu Thr Ser Thr Ser Ser
            1300                1305                1310

Phe Phe Pro Ile Leu Ala Pro Ala Val Gly Ser Tyr Leu Thr Pro Thr Thr Arg
1315                1320                1325                1330

Ala His Ser Pro Ala Ser Leu Ser Phe Ala Ser Tyr Arg Gln Val Ala Ser Phe
            1335                1340                1345                1350

Gly Ser Ala Ala Pro Pro Arg Gln Phe Asp Ala Ser Gln Phe Ser Gln Gly Pro
                1355                1360                1365

Val Pro Gly Thr Cys Ala Asp Trp Ile Pro Gln Ser Ala Ser Cys Pro Thr Gly
    1370                1375                1380                1385

Pro Pro Gln Asn Pro Pro Ser Ala Pro Tyr Cys Gly Ile Val Phe Ser Gly Ser
            1390                1395                1400

Ser Leu Ser Ser Ala Gln Ser Ala Pro Leu Gln His Pro Gly Gly Phe Thr Thr
1405                1410                1415                1420

Arg Pro Ser Ala Gly Thr Phe Pro Glu Leu Asp Ser Pro Gln Leu His Phe Ser
            1425                1430                1435                1440

Leu Pro Thr Asp Pro Asp Pro Ile Arg Gly Phe Gly Ser Tyr His Pro Ser Ala
                1445                1450                1455

Tyr Ser Pro Phe His Phe Gln Pro Ser Ala Ala Ser Leu Thr Ala Asn Leu Arg
    1460                1465                1470                1475

Leu Pro Met Ala Ser Ala Leu Pro Glu Ala Leu Cys Ser Gln Ser Arg Thr Thr
            1480                1485                1490
```

```
-continued

Pro Val Asp Leu Cys Leu Leu Glu Glu Ser Val Gly Ser Leu Glu Gly Ser Arg
1495                1500                1505                1510

Cys Pro Val Phe Ala Phe Gln Ser Ser Asp Thr Glu Ser Asp Glu Leu Ser Glu
        1515                1520                1525                1530

Val Leu Gln Asp Ser Cys Phe Leu Gln Ile Lys Cys Asp Thr Lys Asp Asp Ser
                1535                1540                1545

Ile Pro Cys Phe Leu Glu Leu Lys Glu Glu Asp Glu Ile Val Cys Thr Gln His
    1550                1555                1560                1565

Trp Gln Asp Ala Val Pro Trp Thr Glu Leu Leu Ser Leu Gln Thr Glu Asp Gly
            1570                1575                1580

Phe Trp Lys Leu Thr Pro Glu Leu Gly Leu Ile Leu Asn Leu Asn Thr Asn Gly
1585                1590                1595                1600

Leu His Ser Phe Leu Lys Gln Lys Gly Ile Gln Ser Leu Gly Val Lys Gly Arg
        1605                1610                1615                1620

Glu Cys Leu Leu Asp Leu Ile Ala Thr Met Leu Val Leu Gln Phe Ile Arg Thr
                1625                1630                1635

Arg Leu Glu Lys Glu Gly Ile Val Phe Lys Ser Leu Met Lys Met Asp Asp Pro
        1640                1645                1650                1655

Ser Ile Ser Arg Asn Ile Pro Trp Ala Phe Glu Ala Ile Lys Gln Ala Ser Glu
                1660                1665                1670

Trp Val Arg Arg Thr Glu Gly Gln Tyr Pro Ser Ile Cys Pro Arg Leu Glu Leu
1675                1680                1685                1690

Gly Asn Asp Trp Asp Ser Ala Thr Lys Gln Leu Leu Gly Leu Gln Pro Ile Ser
            1695                1700                1705                1710

Thr Val Ser Pro Leu His Arg Val Leu His Tyr Ser Gln Gly
                1715                1720
```

HUMAN MINOR VAULT PROTEIN P193

STATEMENT REGARDING FEDERALLY SPONSORED RESEARCH OR DEVELOPMENT

The present invention was made with government support under Grant No. GM 38097, awarded by the National Institutes of Health. The United States Government has certain rights in this invention.

BACKGROUND

Cancer is a major cause of morbidity and mortality in the United States. Treatment of cancer generally includes chemotherapy, radiation therapy and surgery. Unfortunately, most cancers cannot be cured using chemotherapy because tumor cells tend to develop resistance to several chemotherapeutic agents over time. These cancers are referred to as "multidrug-resistant cancers" (MDR).

Overexpression of a number of proteins has been found to be associated with MDR cells lines, including P-glycoprotein (Pgp) and multidrug resistance-associated protein (MRP). These proteins appear to mediate drug resistance by acting as cytotoxic drug efflux pumps. However, many MDR cancer cell lines are known which are not associated with overexpression of either P-glycoprotein or multidrug resistance-associated protein.

More recently, a protein has been described that is overexpressed in MDR tumor cell lines which do not overexpress either P-glycoprotein or multidrug resistance-associated protein. This protein was originally named Lung Resistance-related Protein (LRP), referring to the cell line in which it was originally identified. However, once the cDNA for Lung Resistance-related Protein was isolated and the corresponding protein sequence elucidated, it was found that Lung Resistance-related Protein was human major vault protein, a previously known protein.

Vaults are large, barrel-shaped, multi-subunit, cytoplasmic, ribonucleoprotein organelles found in virtually all higher organisms and in most normal tissues. Mammalian vaults consist of three proteins having molecular weights of approximately 210, 193 and 104, and a small RNA in the relative molar ratios of 1:1:24:4 in rats. The most abundant of these, the 104 kDa protein, is termed major vault protein (MVP) and corresponds to the Lung Resistance-related Protein. The minor vault protein p193, however, has not yet been characterized.

Therefore, there remains a need for chemotherapeutic agents that will target multidrug-resistant cancers. Further, there remains a need to characterize the minor vault protein p193.

SUMMARY

According to one embodiment of the present invention, there is provided a protein consisting essentially of purified human minor vault protein p193 or purified biologically active variants thereof, or a combination of purified human minor vault protein p193 and biologically active variants thereof. The protein can be recombinant and can have an amino acid sequence of greater than about 50% identity of the amino acid sequence as set forth in FIG. 2, SEQ ID NO:2. Further, the protein can be a protein recognized by a monoclonal antibody having affinity to any of these proteins.

According to another embodiment of the present invention, there is provided a polynucleotide molecule encoding a protein according to the present invention or its complementary strands, or a polynucleotide molecule which hybridizes to a polynucleotide sequence encoding a protein according to the present invention or its complementary strands. The molecule can be RNA or DNA, or can be another polynucleotide molecule.

According to another embodiment of the present invention, there is provided a vector containing a polynucleotide molecule according to the present invention or a prokaryotic or eukaryotic host cell stably transformed or transfected by the vector.

According to another embodiment of the present invention, there is provided a high affinity monoclonal antibody which immunoreacts with a protein according to the present invention. The antibody can have an Fc portion selected from the group consisting of the IgM class, the IgG class and the IgA class.

According to another embodiment of the present invention, there is provided a method of making a monoclonal antibody which immunoreacts with human minor vault protein p193 comprising the steps of, first, administering human minor vault protein p193 to a host in an amount sufficient to induce the production of antibodies to the human minor vault protein p193 from the antibody-producing cells. Then, the antibody-producing cells are recovered from the host. Next, cell hybrids are formed by fusing the antibody-producing cell to cells capable of substantially unlimited reproduction. Then, the hybrids are cultured. Further, the monoclonal antibodies are collected as a product of the hybrids. The cells capable of substantially unlimited reproduction can be myeloma cells.

According to another embodiment of the present invention, there is provided a method of making a protein according to the present invention comprising the steps of, first, culturing a microorganism transformed with a polynucleotide encoding human minor vault protein p193. Then, the human minor vault protein p193 is recovered.

According to another embodiment of the present invention, there is provided a method of diagnosing a patient with a multidrug-resistant cancer comprising the steps of, first, providing a sample of tissue or fluid from the patient. Then, the level of a substance selected from the group consisting of p193 protein, p193 DNA, p193 mRNA, a substantial portion of p193 protein, a substantial portion of p193 DNA, a substantial portion of p193 mRNA and a combination of one of the foregoing in the patient sample is determined. Next, the level of the substance is compared to a known range of levels for the substance in patients with multidrug-resistant cancers. A diagnosis of multidrug-resistant cancer is made when the level of the substance determined is within the range of levels for the substance in patients with multidrug-resistant cancers. The sample can be selected from the group consisting of bone marrow, cerebral spinal fluid, blood, tears, saliva and a biopsy specimen.

According to another embodiment of the present invention, there is provided a method of treating a patient with multidrug-resistant cancer comprising the steps of, first, diagnosing a patient with multidrug-resistant cancer according to the present invention, and then treating the patient. The treatment can comprise administering to the patient antibodies having an affinity for a substance selected from the group consisting of p193 protein and a polynucleotide encoding p193. The treatment can also comprise administering to the patient at least one antisense polynucleotide having an affinity for a polynucleotide encoding p193. The treatment can further comprise administering to the patient at least one drug that blocks NAD, such as PD128763 and 3-aminobenzamide.

FIGURES

These and other features, aspects and advantages of the present invention will become better understood with regard to the following description, appended claims, and accompanying figures where:

Figure 1A:
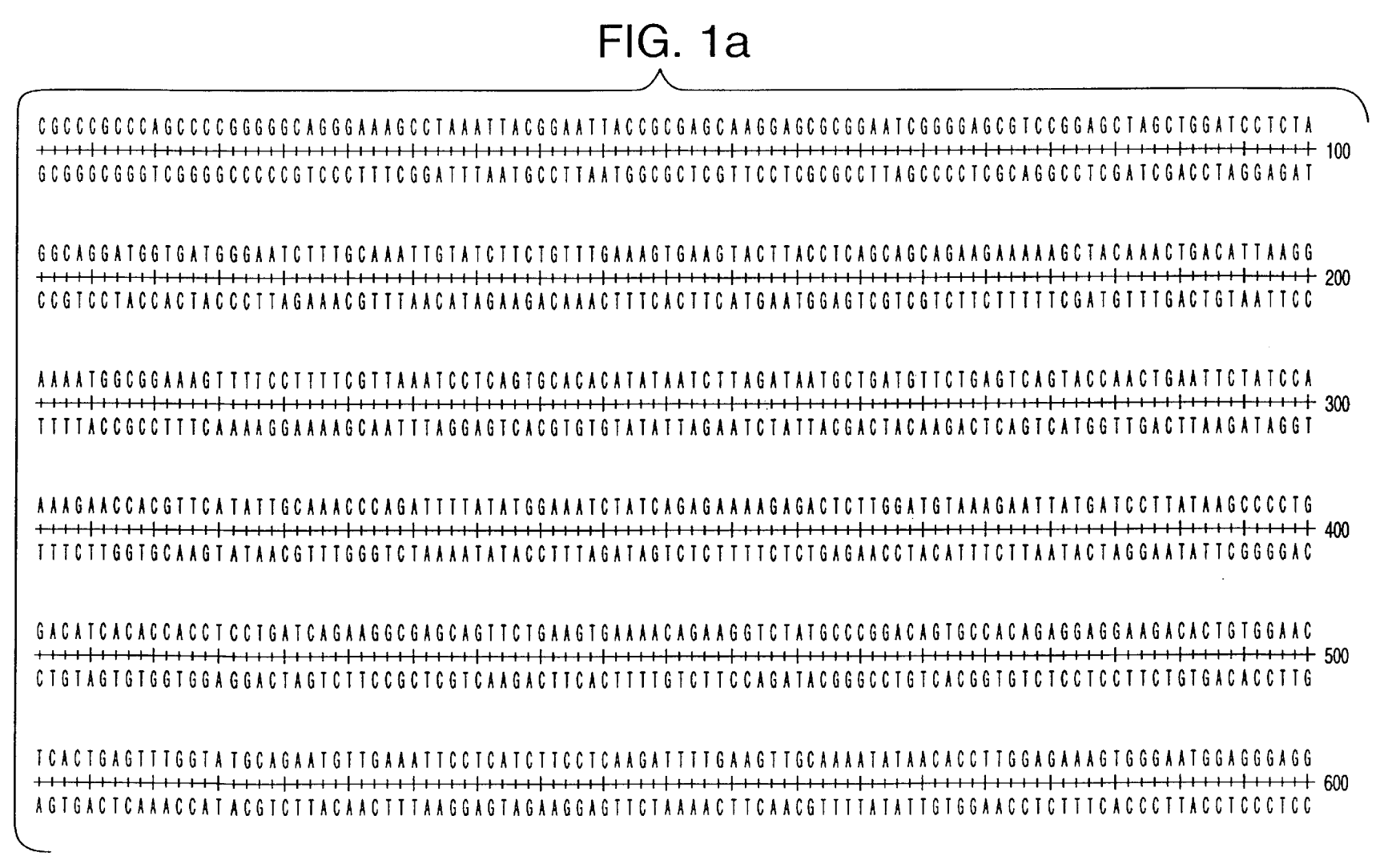
Figure 1B:
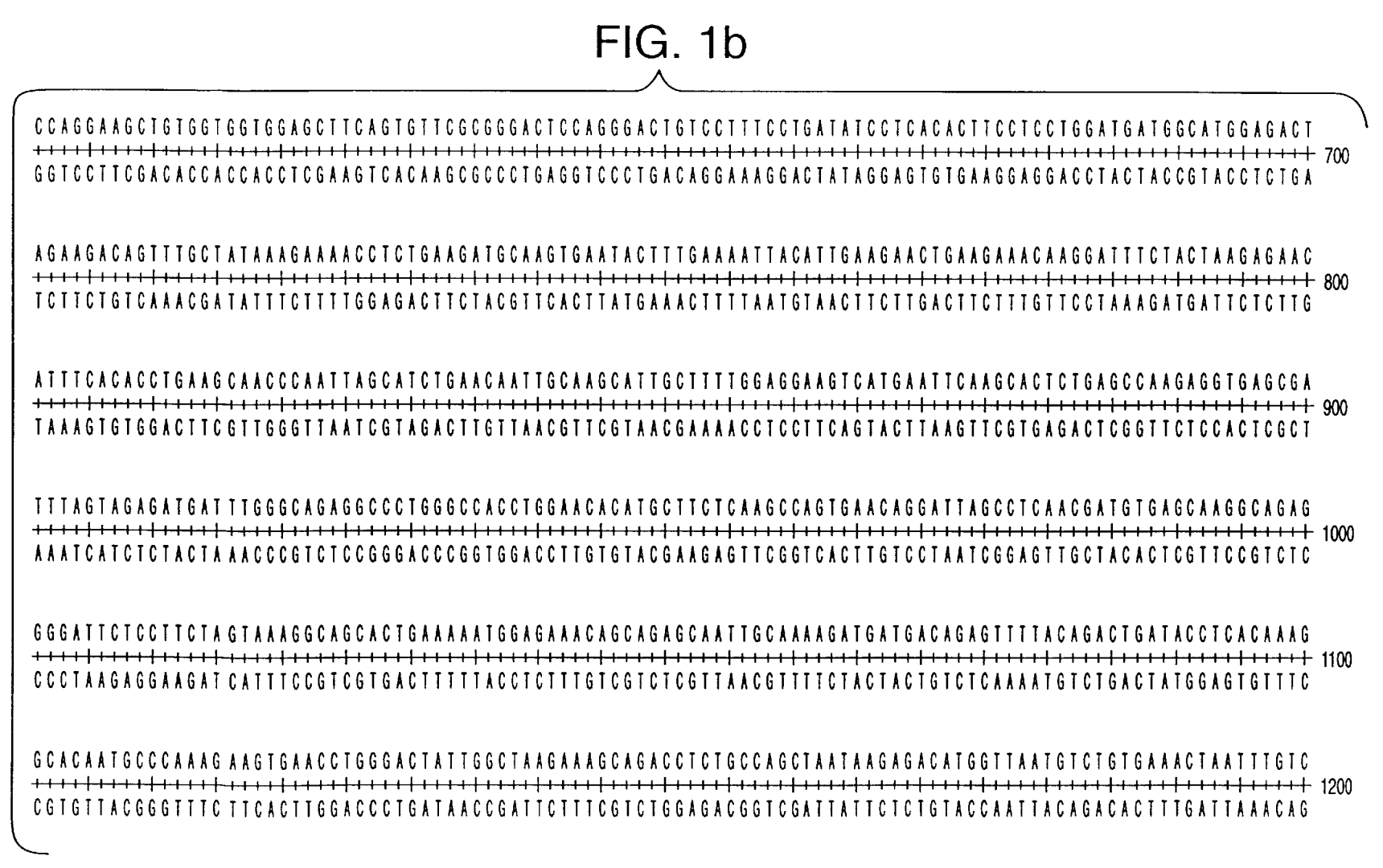
Figure 1C:
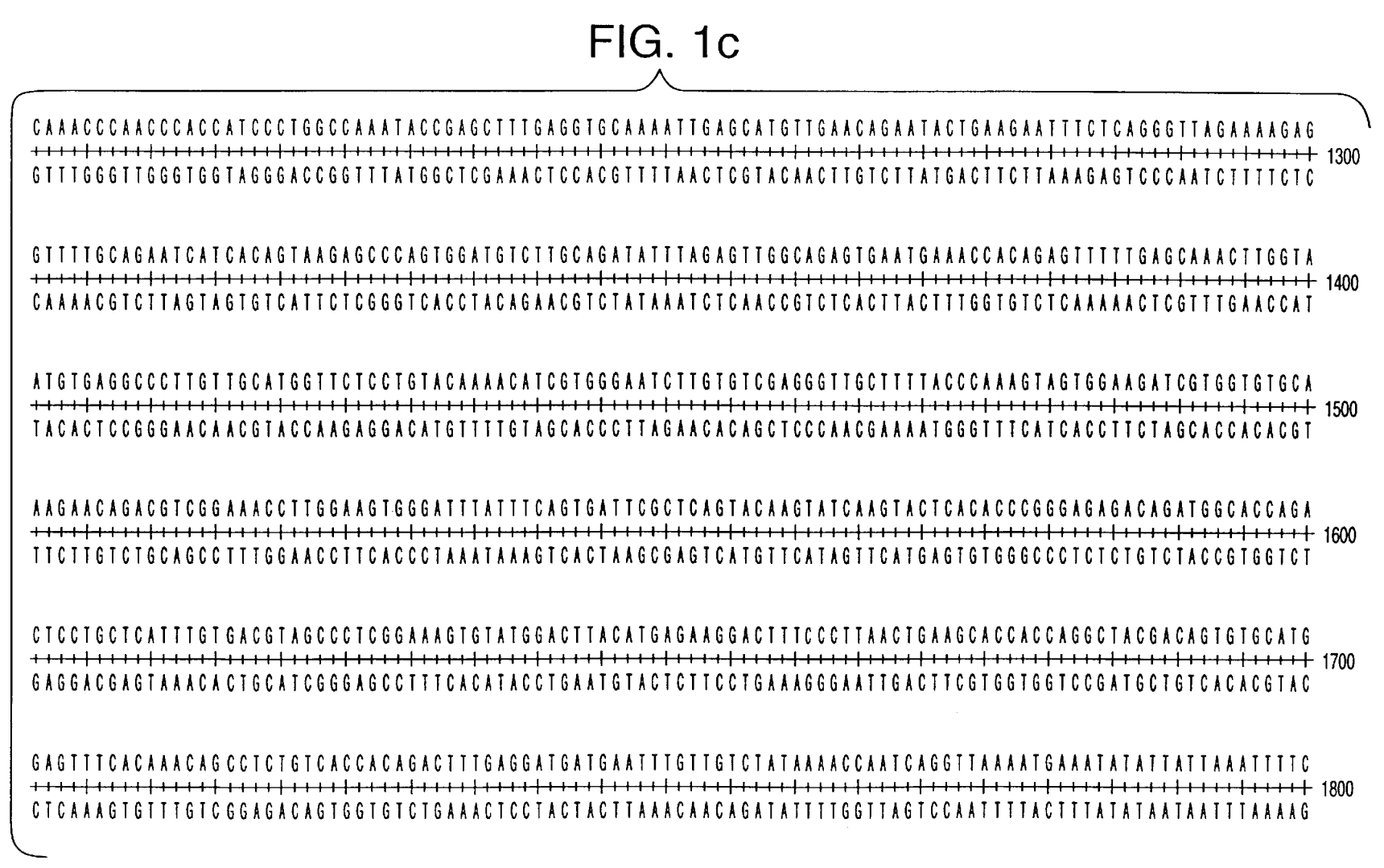
Figure 1D:
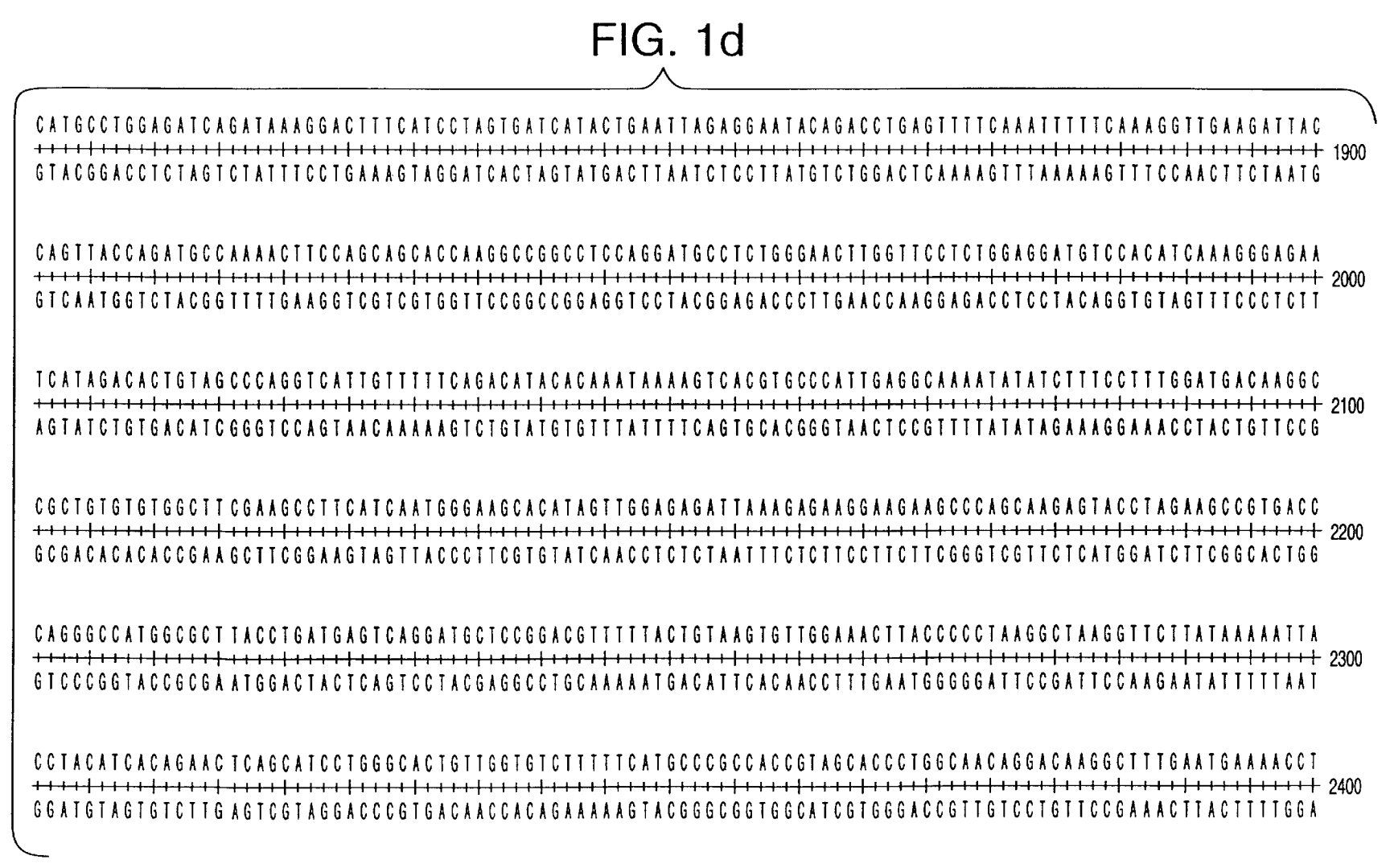
Figure 1E:
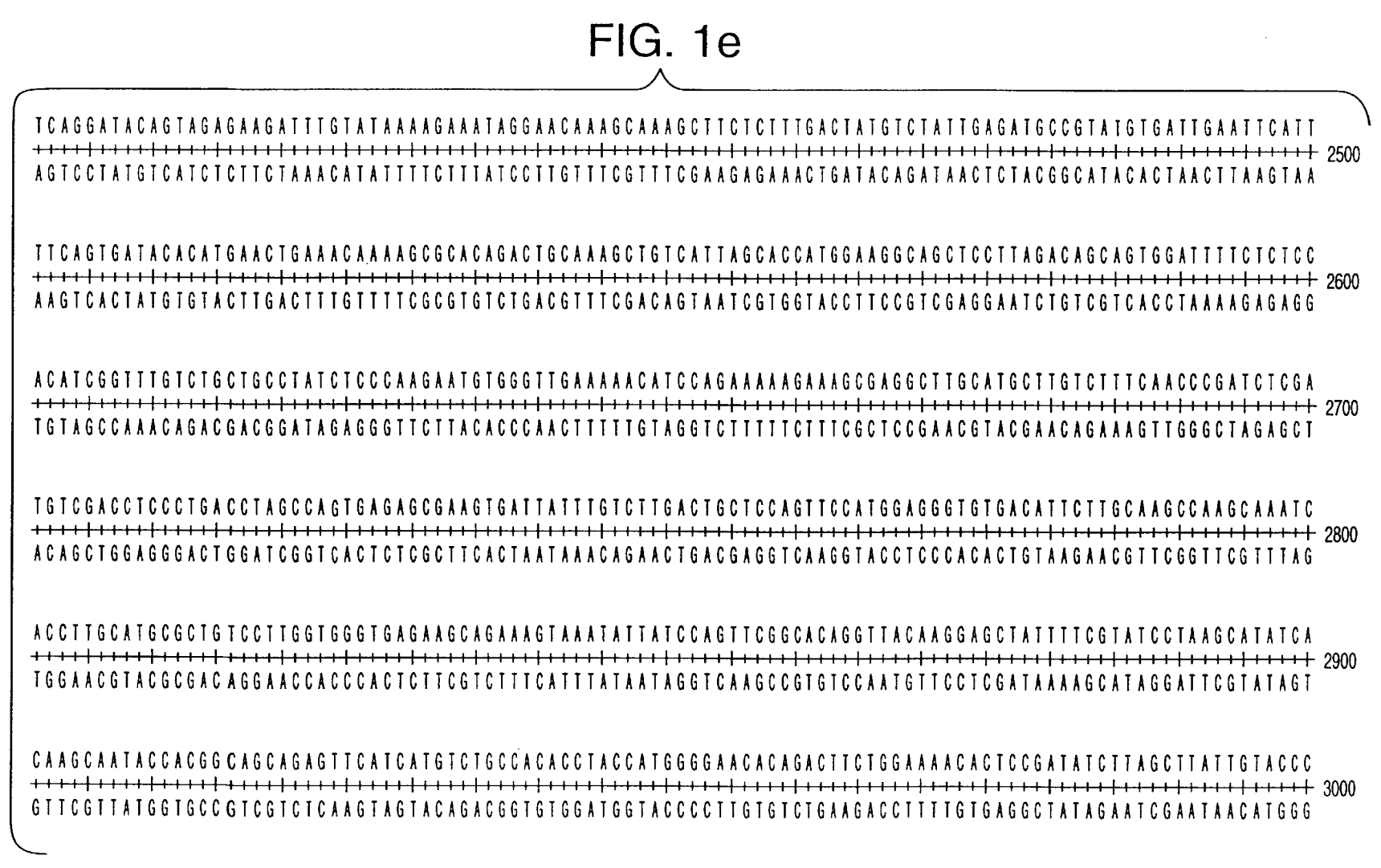
Figure 1F:
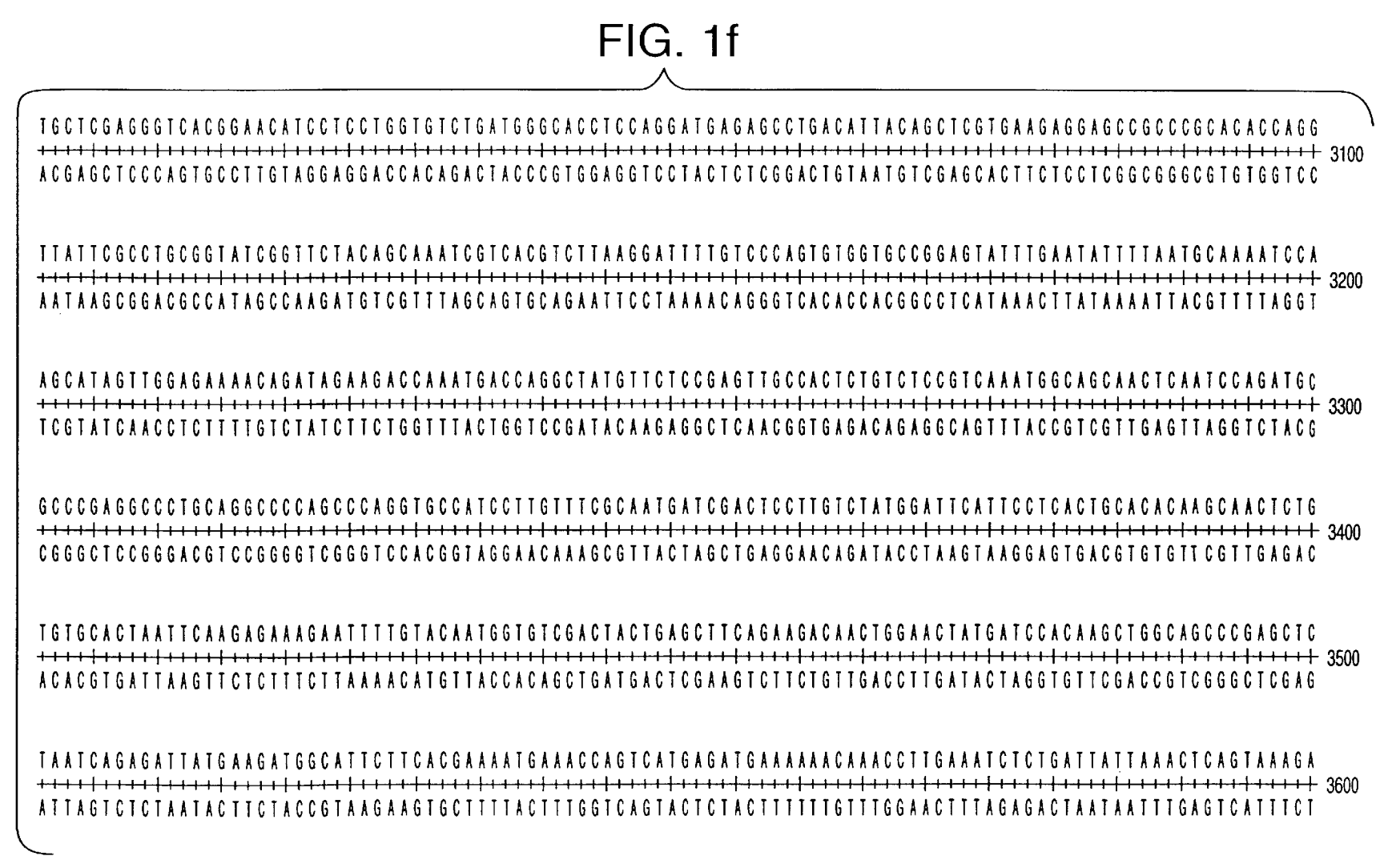
Figure 1G:
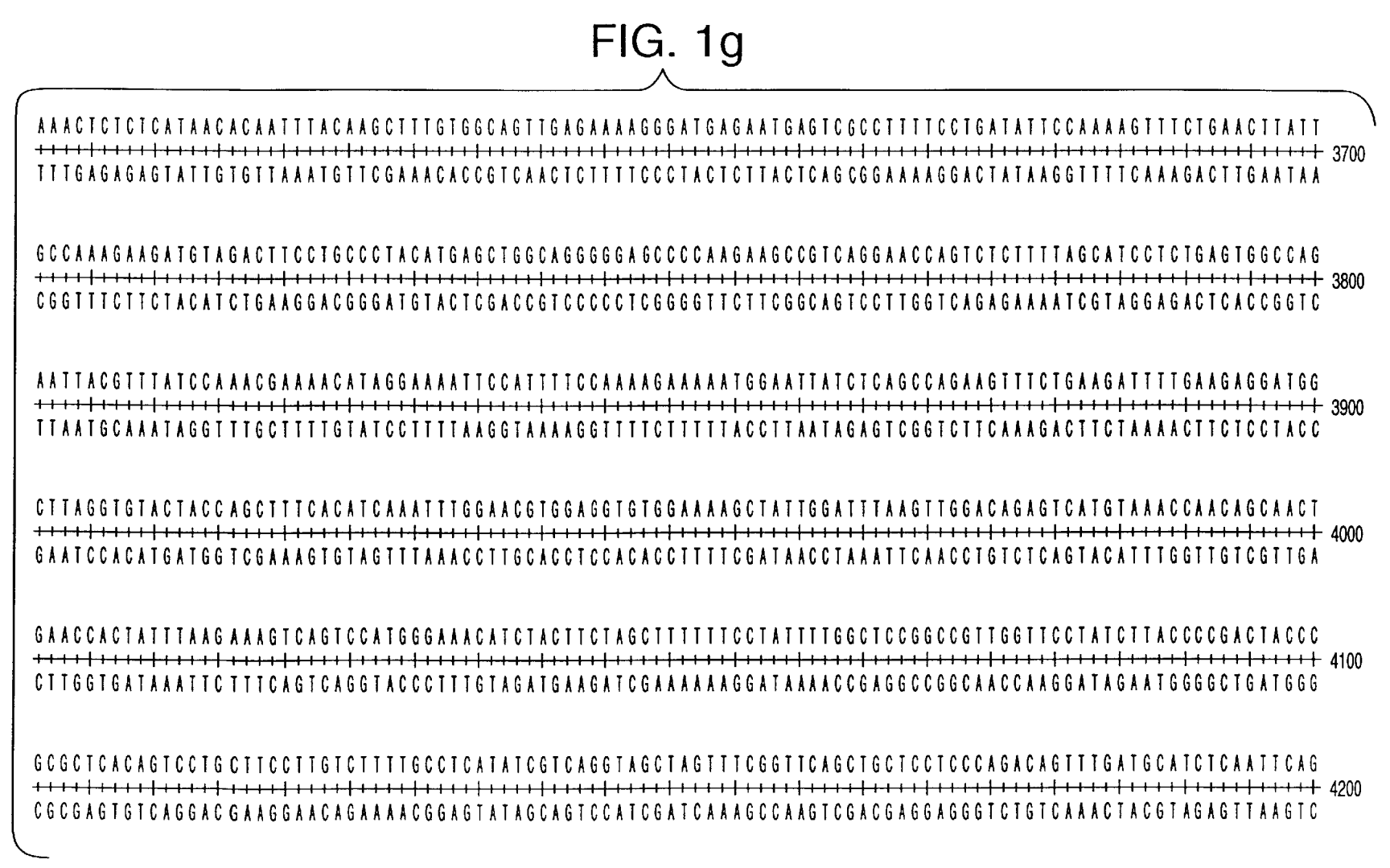

FIGS. 1a–1i show the complete sequence of cDNA encoding human minor vault protein p193, top strand, and its complementary strand; and FIG. 2 shows the complete amino acid sequence of human minor vault protein p193 indicating specific regions of function.

DESCRIPTION

The present invention involves the elucidation of the amino acid sequence for human vault protein p193, as well as the DNA sequence encoding human vault protein p193. These sequences are then utilized in methods of diagnosing multidrug resistance cancer and in methods of treating multidrug resistance cancer.

(1) Elucidation of the Human Minor Vault Protein p193 Amino Acid Sequence and the Nucleotide Sequence Encoding Human Minor Vault Protein p193:

The human minor vault protein p193 amino acid sequence and the nucleotide sequence encoding human minor vault protein p193 were elucidated as follows. First, human vault protein p193 was cloned using an interaction trap, two-hybrid system according to techniques known to those with skill in the art. See, for example, Golemis, et al., *Current Protocols in Mol. Biol.* 20.1.1–20.35 John Willey & Sons, 1997, incorporated by reference in its entirety. In summary, rat major vault protein, GenBank accession number U09870, having the 67 amino acids at the amino-terminal truncated was used as bait against a HeLa acid fusion cDNA library obtained from Roger Brent, Boston, Mass., USA to search for proteins that interacted with rat major vault protein. The interacting proteins were identified by their ability to give rise to blue colonies on media containing galactose and X-gal, a color indicator substrate. The specificity of the interaction between the identified proteins and the rat major vault protein was verified by retransformation of the identified proteins with specific, rat major vault protein and nonspecific (lexA-bicoid) bait cDNAs. This technique identified the cDNA encoding the 193 kDa minor vault protein, SEQ ID NO:1, by its interaction with the rat major vault protein.

Referring now to FIG. 1, there is shown the complete sequence of cDNA encoding human minor vault protein p193, top strand, SEQ ID NO: 1, and its complementary strand. As can be seen, the DNA encoding human minor vault protein p193 contains 5490 base pairs. The open reading frame is from residue 107 to residue 5281.

The cDNA encoding human minor vault protein p193 was then used to deduce the amino acid sequence of the human minor vault protein p193, SEQ ID NO:2. Further, human minor vault protein p193 was purified from vaults by electrophoresis on 5% SDS-polyacrylamide gels. The gels were stained with copper (BioRad Laboratories, Hercules, Calif., USA) and the identified band was excised and destained, and the amino acids sequenced according to standard techniques using a Finmigan TSQ-7000 Triple Quadrupole Mass Spectrometer. This sequence is the same as SEQ ID NO:2.

Referring now to FIG. 2, there is shown the complete amino acid sequence of human minor vault protein p193, SEQ ID NO:2. As can be seen, the sequence includes 1724 amino acid residues.

A search of the National Center for Biotechnology databases was performed to determine if either SEQ ID NO:1 or SEQ ID NO:2 were previously known. The search revealed a previously known nucleotide sequence, GenBank accession number D79999, having 5085 nucleotides which were identical to residues 384–5469 of SEQ ID NO: 1. GenBank accession number D79999 did not, however, include residues 107–383 of SEQ ID NO: 1 which constitutes part of the open reading frame.

The search further revealed that residues 209–563 of SEQ ID NO:2 share 28% identity to residues 609–1004, the catalytic subunit of poly (ADP-ribose) polymerase, GenBank accession number M32721, but did not otherwise reveal a homologous sequence. This catalytic subunit binds to NAD, hydrolyzes the nicotine moiety and polymerizes the ADP ribose group.

Analysis of SEQ ID NO:2 using the PROSITE protein database also revealed that residues 1–94 of SEQ ID NO:2 comprise a BRCT domain. BRCT domains refer to the C-terminus of the cancer susceptibility gene BRCA 1, and are a superfamily of conserved domains in DNA damage-response cell cycle checkpoint proteins. See, for example, Bork, et al., The Faseb J. 11:68–76, 1997; and Callebaut, I. and Mornon, J-P., FEBS Letter 400:25–30, 1997, incorporated by reference in their entirety.

Referring again to FIG. 2, residues 1–94 of human minor vault protein p193, which comprise the BRCT domain, are indicated by the unshaded box. Residues 209–563 of human minor vault protein p193, which share 28% identity to the catalytic subunit of poly (ADP-ribose) polymerase are shown in the upper shaded box. Finally, residues 1562–1724 of human minor vault protein p193, which comprise the region necessary for interaction with human major vault protein, are shown in the lower shaded box.

(2) Generation of Antibodies to Human Minor Vault Protein p193:

Antibodies which immunoreact with human minor vault protein p193 were produced as follows. First, fragments of human minor vault protein p193 were generated using PCR techniques. The fragments consisted of residues 408–611 and residues 1471–1724 of SEQ ID NO:2. Next, fusion proteins were generated and both polyclonal and monoclonal antibodies were produced. These antibodies recognized human minor vault protein p193 in western blots, by immunofluorescence microscopy and by immunoprecipitation.

(3) Description of Certain Embodiments of the Present Invention:

Therefore, according to the present invention, there is provided a protein consisting essentially of purified human minor vault protein p193, SEQ ID NO:2. The protein can also consist of purified biologically active variants of human minor vault protein p193 or a combination of purified human minor vault protein p193, SEQ ID NO:2, and biologically active variants of human minor vault protein p193. In a preferred embodiment, the protein is a recombinant protein. Further, the present invention includes a protein having an amino acid sequence of greater than about 50% identity of the amino acid sequence as set forth in SEQ ID NO:2, as well as a protein recognized by a monoclonal or polyclonal antibody having affinity to a protein according to the present invention.

The protein according to the present invention can be made according to techniques known to those with skill in the art, for example, by first culturing a microorganism transformed with a polynucleotide encoding human minor vault protein p193. Then, the human minor vault protein p193 is recovered from the microorganism.

The present invention also includes a polynucleotide molecule encoding a protein which consists essentially of human minor vault protein p193, SEQ ID NO:2, or biologically active variants of human minor vault protein p193 or a combination of purified human minor vault protein p193, SEQ ID NO:2, and biologically active variants of human minor vault protein p193, such as residues 107 to residue 528 1of SEQ ID NO: 1, and includes the complementary strands to these polynucleotides and a polynucleotide molecule which hybridizes to any of the foregoing polynucleotides. The polynucleotide can be an RNA molecule or a DNA molecule, as well as other polynucleotide molecules.

According to another embodiment of the present invention, there is provided a vector containing a polynucleotide according to the present invention. The vector, such as PET 28 (available from Invitrogen, Carlsbad, Calif., USA), pGEX and pSVL (both available from Amersham Pharmacia Biotech, Piscataway, N.J., USA), can be used to stably transform or transfect a prokaryotic or eukaryotic host cell.

The present invention further includes an antibody which immunoreacts with a protein or polynucleotide according to the present invention. The Fc portion of the antibody can be selected from the group consisting of the IgM class, the IgG class and the IgA class, but can also be other classes. Preferably, the antibody is a high affinity monoclonal antibody which immunoreacts with human minor vault protein p193.

The antibody can be made, for example, by administering human minor vault protein p193 to a host in an amount sufficient to induce the production of antibodies to the human minor vault protein p193 from the antibody-producing cells. Next, the antibody-producing cells are recovered from the host and cell hybrids are formed by fusing the antibody-producing cell to cells capable of substantially unlimited reproduction. Then, the hybrids are cultured and the monoclonal antibodies are collected as a product of the hybrids. Preferably, the cells capable of substantially unlimited reproduction are myeloma cells.

EXAMPLE I

Method of Diagnosing a Patient with a Multidrug-Resistant Cancer

According to one embodiment of the present invention, a patient with a multidrug-resistant cancer is diagnosed by, first, providing a sample of tissue or fluid from the patient. The sample can be bone marrow, cerebral spinal fluid, blood, tears, saliva or a biopsy specimen, or can be other suitable tissue or fluid samples. Next, the level of a substance selected from the group consisting of p193 protein, p193 DNA, p193 mRNA, a substantial portion of p193 protein, a substantial portion of p193 DNA, a substantial portion of p193 mRNA and a combination of one of the foregoing in the patient sample is determined. In a preferred embodiment, the substantial portion comprises at least about 25% of the residues of the molecule. In a particularly preferred embodiment, the substantial portion comprises at least about 50% of the residues of the molecule. Then, the level of the substance is compared to a known range of levels for the substance in patients with multidrug-resistant cancers. A diagnosis of multidrug-resistant cancer is made when the level of the substance determined is within the range of levels for the substance in patients with multidrug-resistant cancers.

EXAMPLE II

Method of Treating a Patient with Multidrug-Resistant Cancer

According to another embodiment of the present invention, a patient with a multidrug-resistant cancer is treated by disrupting the production or function of human minor vault protein p193. This is accomplished by, for example, administering to the patient antibodies having an affinity for a substance selected from the group consisting of p193 protein and a polynucleotide encoding p193. Treatment can also be accomplished by administering to the patient at least one antisense polynucleotide having an affinity for a polynucleotide encoding p193. Further, treatment can be accomplished by administering to the patient at least one drug that blocks NAD, such as PD128763 and 3-aminobenzamide.

Although the present invention has been discussed in considerable detail with reference to certain preferred embodiments, other embodiments are possible. Therefore, the spirit and scope of the appended claims should not be limited to the description of preferred embodiments contained in this application.

What is claimed is:

1. A purified protein comprising an amino acid sequence as set forth in SEQ ID NO:2.

2. A composition consisting essentially of the protein according to claim 1.

3. A composition comprising of the protein according to claim 1.

4. An isolated protein comprising an amino acid sequence as set forth in SEQ ID NO:2.

5. A composition consisting essentially of the protein according to claim 4.

6. A composition comprising the protein according to claim 4.

7. A method of catalyzing the hydrolysis of the nicotine moiety or of catalyzing the polymerization of the ADP ribose group of at least one NAD molecule comprising contacting the NAD molecule with the protein according to claim 1.

8. A method of diagnosing a patient with a multidrug-resistant cancer comprising:
   (a) providing a sample of tissue or fluid from the patient;
   (b) determining the level of the protein as set forth in claim 1; and
   (c) comparing the level of the protein to a known range of levels for the substance in patients with multidrug-resistant cancers,
wherein a diagnosis of multidrug-resistant cancer is made when the level of the protein is within the range of levels for the protein in patients with multidrug-resistant cancers.

9. The method of claim 8, wherein the sample is selected from the group consisting of bone marrow, cerebral spinal fluid, blood, tears, saliva and a biopsy specimen.

10. A method of treating a patient with multidrug-resistant cancer comprising:
   (a) diagnosing a patient with multidrug-resistant cancer according to claim 8; and
   (b) treating the patient.

11. A method of diagnosing a patient with a multidrug-resistant cancer comprising:
   (a) providing a sample of tissue or fluid from the patient;
   (b) determining the level of the protein as set forth in claim 4; and
   (c) comparing the level of the protein to a known range of levels for the substance in patients with multidrug-resistant cancers,
wherein a diagnosis of multidrug-resistant cancer is made when the level of the protein is within the range of levels for the protein in patients with multidrug-resistant cancers.

12. The method of claim 11, wherein the sample is selected from the group consisting of bone marrow, cerebral spinal fluid, blood, tears, saliva and a biopsy specimen.

13. A method of treating a patient with multidrug-resistant cancer comprising:
   (a) diagnosing a patient with multidrug-resistant cancer according to claim 11; and
   (b) treating the patient.

14. A method of catalyzing the hydrolysis of the nicotine moiety or of catalyzing the polymerization of the ADP ribose group of at least one NAD molecule comprising contacting the NAD molecule with the protein accounting to claim 4.

* * * * *